(12) United States Patent
Lin et al.

(10) Patent No.: US 8,699,870 B2
(45) Date of Patent: Apr. 15, 2014

(54) VEHICULAR EYE-CONTROLLED DEVICE HAVING ILLUMINATION LIGHT SOURCE

(75) Inventors: Po-Tsung Lin, New Taipei (TW); Ming-Chen Lai, New Taipei (TW); Hung-Ju Tsai, New Taipei (TW); Yu-Ling Tang, New Taipei (TW)

(73) Assignee: Utechzone Co., Ltd., New Taipei (TW)

( * ) Notice: Subject to any disclaimer, the term of this patent is extended or adjusted under 35 U.S.C. 154(b) by 113 days.

(21) Appl. No.: 13/434,036

(22) Filed: Mar. 29, 2012

(65) Prior Publication Data

US 2013/0259460 A1 Oct. 3, 2013

(51) Int. Cl.
*G03B 15/03* (2006.01)
*G03B 17/00* (2006.01)
*G03B 19/00* (2006.01)
*B60Q 1/00* (2006.01)

(52) U.S. Cl.
USPC ............. 396/155; 396/51; 396/429; 340/439; 340/937

(58) Field of Classification Search
USPC .................... 396/155, 429, 51; 340/439, 937; 382/117
See application file for complete search history.

(56) References Cited

U.S. PATENT DOCUMENTS

2008/0089559 A1* 4/2008 Koumura ....................... 382/117
2009/0066065 A1* 3/2009 Breed et al. .................... 280/735

FOREIGN PATENT DOCUMENTS

CN 102069710 5/2011

OTHER PUBLICATIONS

J.S. Babcock et al., "Building a lightweight eyetracking headgear," Rochester Institute of Technology, Association for Computing Machinery, Inc., 2004, pp. 109-113.

* cited by examiner

*Primary Examiner* — Rochelle-Ann J Blackman
(74) *Attorney, Agent, or Firm* — Morris, Manning & Martin, LLP; Juan Carlos A. Marquez

(57) ABSTRACT

A vehicular eye-controlled device having an illumination light source essentially includes a first body and a second body which are independent and separate. The first body has an electronic component disposed therein and required for operation and a photographic unit exposed therefrom for capturing an image of a driver. The second body is disposed in the vicinity of the first body and includes an illumination unit for providing illumination required for eye-controlled operation. The illumination unit and the photographic unit are separated by a distance of at least 5 cm.

6 Claims, 2 Drawing Sheets

VEHICULAR EYE-CONTROLLED DEVICE HAVING ILLUMINATION LIGHT SOURCE

BACKGROUND OF THE INVENTION

1. Technical Field

The present invention relates to eye-controlled devices, and more particularly, to a vehicular eye-controlled device equipped with an illumination light source and characterized by separation light source design.

2. Description of Related Art

Enhancement of road safety is an increasingly important issue recently and thus is one of the focuses of the search performed by related manufacturers. Traffic accidents are caused mostly by faulty driving. Causes of faulty driving include fatigue resulting from inadequate sleep, lengthy driving with an insufficient break, cell phone use while driving, or drunk driving. That is to say, being of unsound mind, such as being overly relaxed or paying little attention, is the major cause of traffic accidents.

To solve the aforesaid problems, various technical solutions are put forth, including China's patent application No. 200910310326.3 entitled "Driving Monitoring Device and Method" and directed to capturing images to detect a driver's visual field and the driver's hands at a steering wheel and determine whether the driver's hands are at a correction region of the steering wheel and whether the driver's eyes are open or are shut due to fatigue.

Jason S. babcock & Jeff B. Pelz from Rochester Institute of technology put forth "Building a lightweight eyetracking headgear" which discloses a lightweight eyetracking device for positioning a camcorder at an eyeglasses frame to detect eyeball movement and thereby enable various applications.

It is feasible and advantageous to monitor visual condition in order to prevent fatigue-induced traffic accidents or obtain eyeball movement parameters in order to perform medical behavior or scientific research. However, in practice, this kind of technology requires capturing eyeball images to analyze and judge them but is seldom free of bad judgment or failure. It is because the major measures taken according to this kind of technology entails capturing eyeball images with the camcorder, irradiating the eyeballs with an IR LED lamp, such that a light spot is formed on the eyeball surface by reflection, thereby determining the position of the light spot relative to the pupil so as to calculate eyeball movement parameters. A key to the aforesaid technology lies in illumination based on an IR LED. A short distance between the light spot and the pupil or inappropriate illumination that ends up shifting the light spot or even producing no light spot at all prevents eyeball movement from being judged; as a result, the device fails.

SUMMARY OF THE INVENTION

In view of this, the present invention provides a vehicular eye-controlled device having an illumination light source to enable accurate illumination operation and produce an appropriate light spot on the eyeball surface, thereby greatly boosting the accuracy of judgment performed with the eye-controlled device and overcoming the drawbacks of a conventional device, such as bad judgment or failure.

As disclosed in the present invention, a vehicular eye-controlled device having an illumination light source essentially comprises a first body and a second body which are independent of each other. The first body has an electronic component disposed therein and required for operation and a photographic unit exposed from a side of the first body for capturing an image. The second body is disposed in vicinity of the first body and equipped with an illumination unit for providing illumination to a driver's eyes. The illumination unit and the photographic unit are separated by a distance of at least 5 cm.

BRIEF DESCRIPTION OF THE SEVERAL VIEWS OF THE DRAWINGS

Objectives, technical contents, and features of the present invention are hereunder illustrated with a preferred embodiment in conjunction with the accompanying drawings, in which.

DETAILED DESCRIPTION OF THE EMBODIMENT OF THE INVENTION

Figure 1:
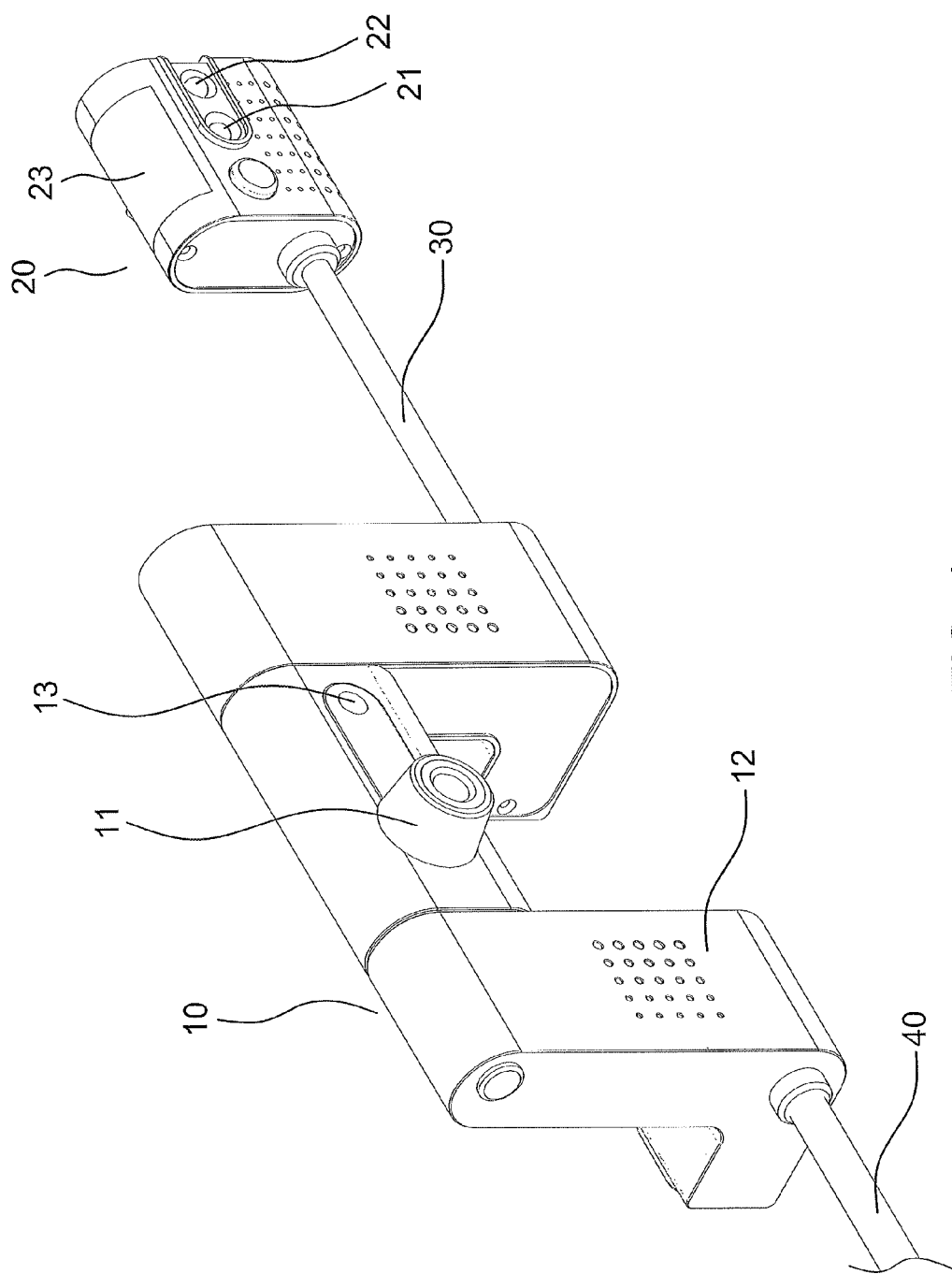
FIG. 1 is a perspective schematic view of a vehicular eye-controlled device having an illumination light source according to a preferred embodiment of the present invention.
Figure 2:
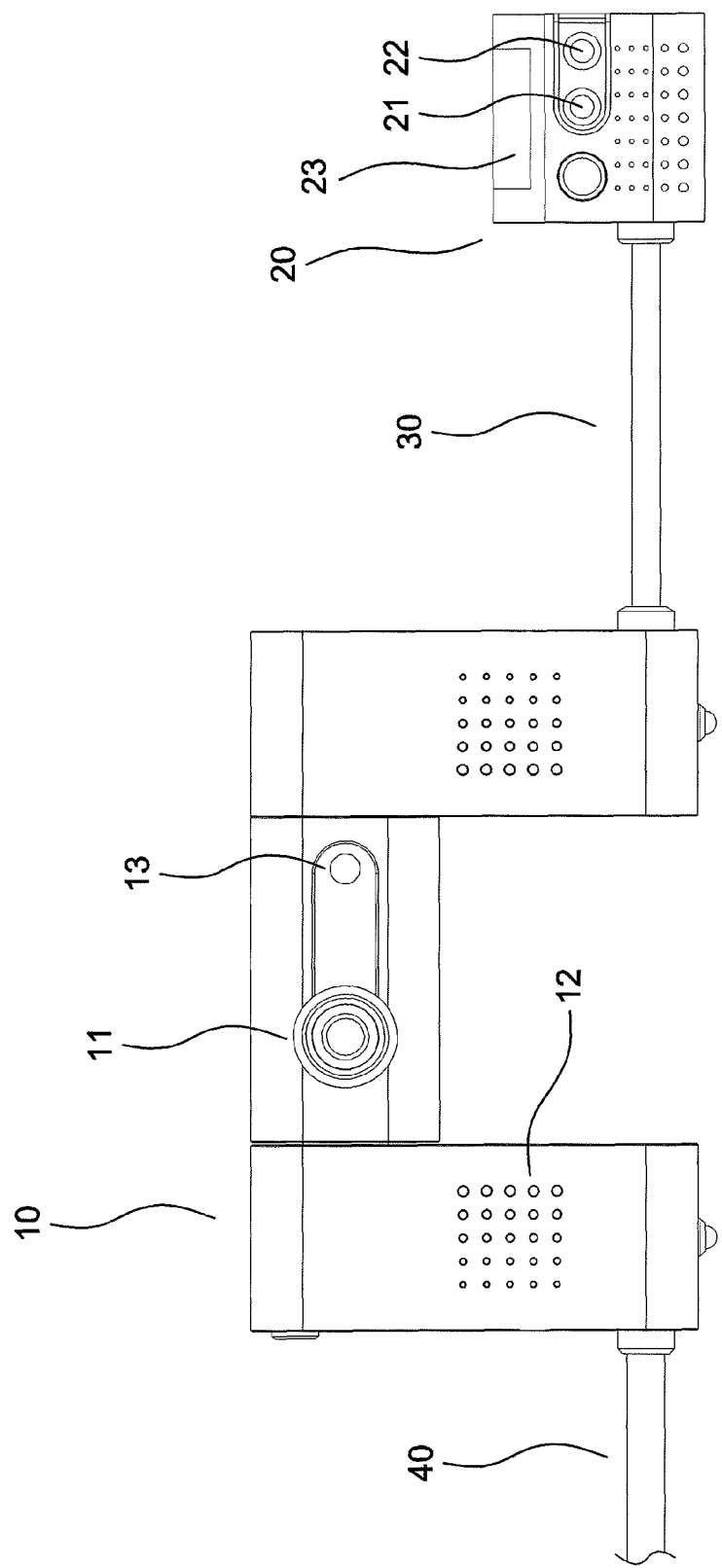
FIG. 2 is a front view of the vehicular eye-controlled device having an illumination light source according to a preferred embodiment of the present invention.

Referring to FIG. 1 and FIG. 2, there are shown schematic views of a vehicular eye-controlled device having an illumination light source according to a preferred embodiment of the present invention. The vehicular eye-controlled device essentially includes a first body 10 and a second body 20 which are independent and separate. A photographic unit 11 which is exposed, a sound generating unit 12, and a control button 13 are disposed at the first body 10. The photographic unit 11 captures images of a driver's eyeballs and transmits the images to an electronic component (not shown) accommodated in the first body 10 for performing image computation and processing or various system control. The sound generating unit 12 generates a sound based on a command from the device. A user can turn on or off the power to the device with the control button 13. The first body 10 has a second transmission line 40 for connecting with an external apparatus, for transmitting data to and from the external apparatus, or for controlling the data thus transmitted. In addition to the aforesaid means of wired connection adapted for communication with the outside, the first body 10 has a Wi-Fi or 3G wireless communication unit (not shown) optionally disposed therein for transmitting data to and from the external apparatus by means of wireless transmission. The drawings of the present invention are illustrative rather than restrictive of the way of transmitting data.

A first illumination unit 21, a second illumination unit 22, and an alert unit 23 are disposed at the second body 20. The first body 10 and the second body 20 send data to each other via a first transmission line 30. The first illumination unit 21 and the second illumination unit 22 provide illumination to the user's eyes. The aforesaid illumination units are IR LEDs for irradiating the user's eyes to produce light spots. Alternatively, the aforesaid illumination units are white. LEDs for providing auxiliary illumination. The alert unit 23 is positioned at the top of the second body 20 for giving an alert based on a control command from the device.

Since the first body 10 and the second body 20 are independent of each other and thus their positions can be adjusted as needed, and they can transmit data to each other via the first transmission line 30. Preferably, the illumination units disposed at the second body 20 are separated from the photographic unit 11 by a distance of at least 5 cm, so as to preclude a short distance between a light spot on the driver's eyeball surface and the driver's eye pupils or severe deviation that compromises judgment. According to the present invention, images of the driver's eyeballs are capture and accurately analyzed and judged, so as to boost the accuracy of judgment of eyeball images greatly.

Although the present invention is disclosed above by preferred embodiments, the preferred embodiments are not restrictive of the present invention. Hence, persons skilled in the art can make changes and modifications to the preferred embodiments without departing from the spirit and scope of the present invention. Accordingly, the legal protection for the present invention should be defined by the appended claims.

What is claimed is:

1. A vehicular eye-controlled device having an illumination light source, comprising:
    a first casing having an electronic component disposed therein, a photographic unit exposed from a side of the first casing for capturing an image of a driver's eyeballs and transmitting the image to the electronic component for performing image computation, and a control button exposed from the side of the first casing for turning on or off power to the vehicular eye-controlled device; and
    a second casing disposed in vicinity of the first casing and equipped with an illumination unit that comprises a first illumination unit and a second illumination unit for providing illumination to the driver's eyeballs to produce light spots, wherein the illumination unit and the photographic unit of the first casing are separated by 5 cm.

2. The vehicular eye-controlled device of claim 1, further comprising a sound generating unit disposed at the first casing for generating a sound.

3. The vehicular eye-controlled device of claim 1, further comprising an alert unit disposed at the second casing for giving an alert based on a command.

4. The vehicular eye-controlled device of claim 1, further comprising a transmission line connected to the first casing for transmitting data to and from outside.

5. The vehicular eye-controlled device of claim 1, wherein a transmission line for interconnect is disposed between the first casing and the second casing to enable data transmission operation.

6. The vehicular eye-controlled device of claim 1, wherein the first casing comprises a wireless communication unit for transmitting data by means of wireless transmission.

* * * * *